United States Patent
Shkolnikov et al.

(10) Patent No.: US 11,577,252 B2
(45) Date of Patent: *Feb. 14, 2023

(54) THERMALLY CONTROLLED REAGENT RELEASE

(71) Applicant: HEWLETT-PACKARD DEVELOPMENT COMPANY, L.P., Spring, TX (US)

(72) Inventors: Viktor Shkolnikov, Palo Alto, CA (US); Chien-Hua Chen, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/605,780

(22) PCT Filed: Apr. 27, 2018

(86) PCT No.: PCT/US2018/029737
§ 371 (c)(1),
(2) Date: Oct. 16, 2019

(87) PCT Pub. No.: WO2019/209308
PCT Pub. Date: Oct. 31, 2019

(65) Prior Publication Data
US 2021/0322990 A1 Oct. 21, 2021

(51) Int. Cl.
*B01L 3/00* (2006.01)
*B01L 7/00* (2006.01)
*G01N 33/543* (2006.01)

(52) U.S. Cl.
CPC ............ *B01L 7/52* (2013.01); *B01L 3/502761* (2013.01); *G01N 33/54386* (2013.01);
(Continued)

(58) Field of Classification Search
None
See application file for complete search history.

(56) References Cited

U.S. PATENT DOCUMENTS

| 6,613,581 B1 | 9/2003 | Wada et al. |
| 2002/0092767 A1 | 7/2002 | Bjornson et al. |

(Continued)

FOREIGN PATENT DOCUMENTS

CN 106957788 A 7/2017

OTHER PUBLICATIONS

Hitzbleck M. et al. Reagents in microfluidics: an in and out challenge. Chem. Soc. Rev. 2013. vol. 42. p. 8494-8516.
(Continued)

*Primary Examiner* — Rebecca M Giere
(74) *Attorney, Agent, or Firm* — Foley & Lardner LLP (57) ABSTRACT

An example system includes an array of retaining features in a microfluidic cavity, an array of thermally controlled releasing features, and a controller coupled to each releasing feature in the array of releasing feature. Each retaining feature in the array of retaining features is to position capsules at a predetermined location, the capsules having a thermally degradable shell enclosing a biological reagent therein. Each releasing feature in the array of releasing features corresponds to a retaining feature and is to selectively cause degradation of the shell of a capsule. Each releasing feature is to generate thermal energy to facilitate degradation of the shell. The controller is to selectively activate at least one releasing feature in the array of thermally controlled releasing features to release the biological reagent in the capsules positioned at the retaining feature corresponding to the activated releasing feature.

15 Claims, 9 Drawing Sheets

(52) U.S. Cl.
CPC ..... *B01L 2300/12* (2013.01); *B01L 2300/165* (2013.01); *B01L 2300/1827* (2013.01); *B01L 2400/0424* (2013.01); *B01L 2400/086* (2013.01)

(56) References Cited

U.S. PATENT DOCUMENTS

| | | | |
|---|---|---|---|
| 2004/0214056 A1* | 10/2004 | Gore | C01B 3/065 422/198 |
| 2006/0228734 A1* | 10/2006 | Vann | G01N 21/6428 435/6.19 |
| 2009/0143233 A1 | 6/2009 | Knight et al. | |
| 2014/0155295 A1 | 6/2014 | Hindson et al. | |
| 2017/0058324 A1 | 3/2017 | Balog et al. | |

OTHER PUBLICATIONS

Mauk M.G. et al. Simple Approaches to Minimally-Instrumented, Microfluidic-Based Point-of-Care Nucleic Acid Amplification Tests. Biosensors. 2018 (Published: Feb. 26, 2018). vol.8, No. 17.

Wang T. et al. Ultrasensitive microfluidic solid-phase ELISA using an actuatable microwell-patterned PDMS chip. Lab Chip. 2013. vol.13, Iss.21, p. 4190-4197.

\* cited by examiner

THERMALLY CONTROLLED REAGENT RELEASE

BACKGROUND

Microfluidic devices are increasingly commonplace in a variety of environments. For example, microfluidic devices have applicability in biology, medicine, genetics and numerous other fields. Microfluidic devices may include such devices as lab-on-a-chip micro-total analytical systems and can carry, analyze, or process various particles, bacteria, biological cells and other solid and soft objects of microscale. Various microfluidic devices may include fluids flowing through narrow channels. In a lab-on-a-chip, for example, blood cells may be moved from one chamber to another, such as from an input port to a reaction chamber. In other examples, the microfluidic device may be provided for the flow of other fluids or materials, such as blood or other biological fluids.

BRIEF DESCRIPTION OF THE DRAWINGS

For a more complete understanding of various examples, reference is now made to the following description taken in connection with the accompanying drawings in which.

DETAILED DESCRIPTION

As noted above, microfluidic devices may include fluids flowing through narrow channels. In various examples, the fluids may include reagents or other material to be released when desired. For example, an antibody or a nucleic acid segment may be released into a flow for testing or to facilitate testing. Such microfluidic devices may be used to test a large number of targets, such as nucleic acid segments, antigens or the like. Thus, microfluidic devices may be formed for specific set of targets or may call upon an operator to manually configure the devices for a particular set of targets.

Various examples described herein relate to detection or testing of nucleic acid segments. In various examples, various types of reagents may be stored, or retained, in an array using an array of retaining features. An array of releasing features is provided with releasing features corresponding to each retaining feature in the array of retaining features. The reagents are stored in a capsule with a thermally degradable shell surrounding the reagent, with the capsules being retained by the retaining features. When a nucleic acid is to be processed, a releasing feature is actuated to release a corresponding reagent. In various examples, the retaining features include physical barriers such as pillars, weirs, meshes, magnetic portions, or other features which facilitate positioning of the capsules. The releasing features, such as resistors, generate thermal energy to degrade the shell of a selected capsule to cause release of the reagent. The reagent and the nucleic acid segment are passed through a thermocycling region to cause amplification of the nucleic acid segment. Various nucleic acid segments may be processed in sequence, with corresponding reagents being released in sequence corresponding to the nucleic acid segments. Thus, various examples described herein provide microfluidic devices that may be configured or reconfigured as desired for testing of a large variety of targets.

Figure 1:
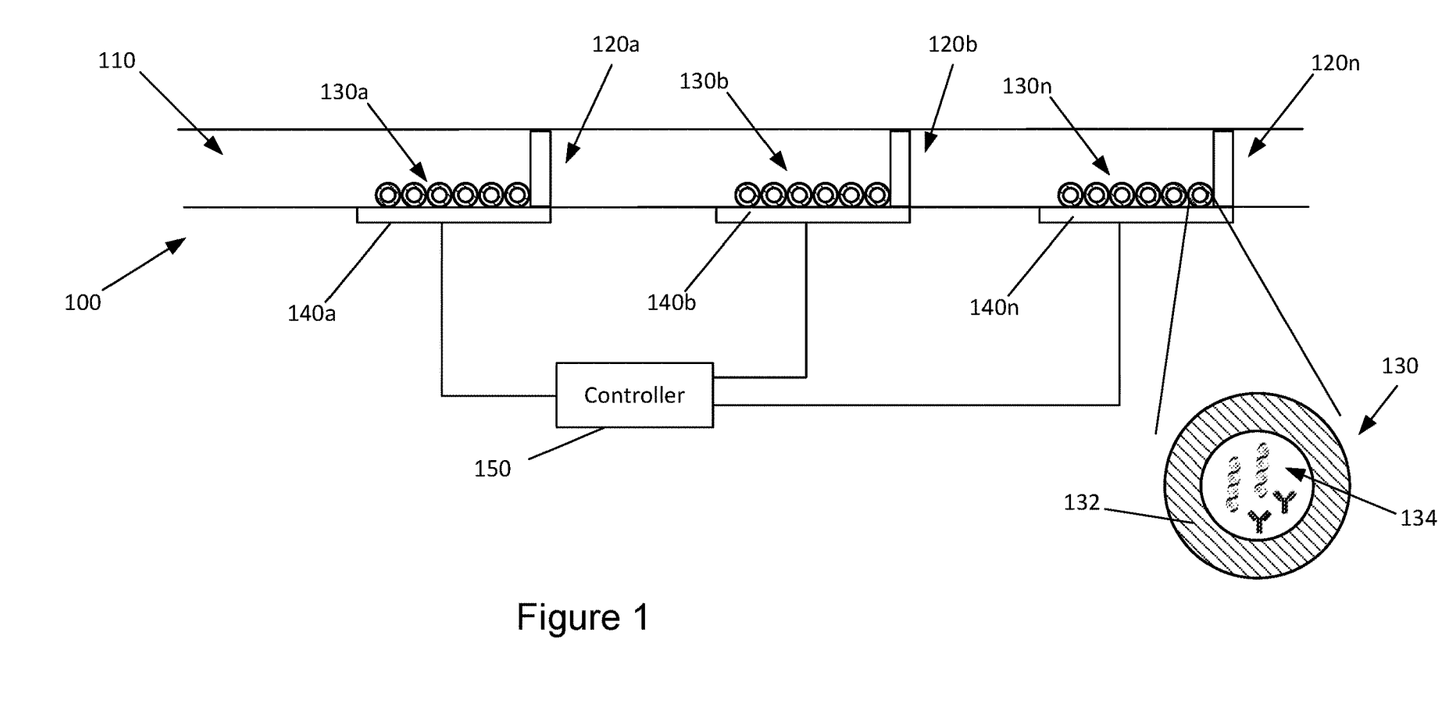
FIG. 1 illustrates an example system for selective release of material in thermally degradable capsules.

Referring now to the Figures, FIG. 1 illustrates an example system 100 for selective release of material in thermally degradable capsules. In various examples, the example system 100 may be implemented as a lab-on-a-chip or a part thereof. The example system 100 of FIG. 1 includes a microfluidic cavity 110 which may accommodate particles or fluid therein. In one example, the cavity 110 is a microfluidic channel with a cross-sectional width of between about 10 μm and about 500 μm.

The example system 100 is provided with an array of retaining features 120a-n within the microfluidic cavity 110. The example system 100 of FIG. 1 is illustrated with three retaining features 120, but any practical number is possible and contemplated within the scope of the present disclosure. Each retaining feature 120a-n is provided to position capsules 130a-c at a predetermined location in the microfluidic cavity 110. As illustrated in the example of FIG. 1, the capsules 130 include a shell 132 enclosing material 134 therein. The shell 132 is formed of a thermally degradable material, such as wax or a polymer. The thermally degradable material may be selected based on a variety of factors, such as the melting point of the thermally degradable material. In various examples, the thermally degradable material used for the shell 132 may be icosane ($C_{20}H_{42}$), triacontane ($C_{30}H_{62}$), tetracontane ($C_{40}H_{82}$), pentacontane ($C_{50}H_{102}$), hexacontane ($C_{60}H_{122}$), or a combination thereof. The material 134 in the shell 132 may include any of a variety of materials such as a reagent, antibody, nucleic acid fragment, or a combination thereof, for example. In various examples, the material 134 may be provided in an aqueous solution.

In various examples, as described below, each retaining feature 120a-n may be a mechanical barrier sized to prevent flow of the capsules 130a-n through the barrier. The retaining features 120a-n may be provided with openings or spacing to allow flow of the material 134 through the microfluidic cavity when the material 134 is released from the capsule 130. Various examples of retaining feature 120 are described below with reference to FIGS. 2-4. In other examples, the retaining feature 120a-n may be implemented as a non-mechanical feature, examples of which are described below with reference to FIGS. 5-7.

To facilitate release of the material 134 from the capsules 130, the example system 100 of FIG. 1 is provided with an array of thermally controlled releasing features 140a-n. Each releasing feature 140a-n of FIG. 1 is to selectively cause degradation of the shell 132 of the capsule 130, thus releasing the material 134 into the microfluidic cavity 110. In this regard, the releasing feature 140a-n generates thermal energy (e.g., heat) to facilitate degradation of the shell 132, with the shell 132 formed of a thermally degradable material. The releasing feature 140a-n of the example system 100 of FIG. 1 is positioned adjacent to a corresponding retaining feature 120a-n substantially at the predetermined position for retaining the capsules.

The example system 100 of FIG. 1 further includes a controller 150 coupled to each releasing feature 140a-n in the array of thermally controlled releasing features. The controller 150 may selectively activate at least one releasing feature 140a-n in the array to degrade the shell 132 of the corresponding cells and to release the material 134 (e.g., biological reagent) in the capsules 130a-n positioned at the retaining feature 120a-n corresponding to the activated releasing feature 140a-n.

Figure 2:
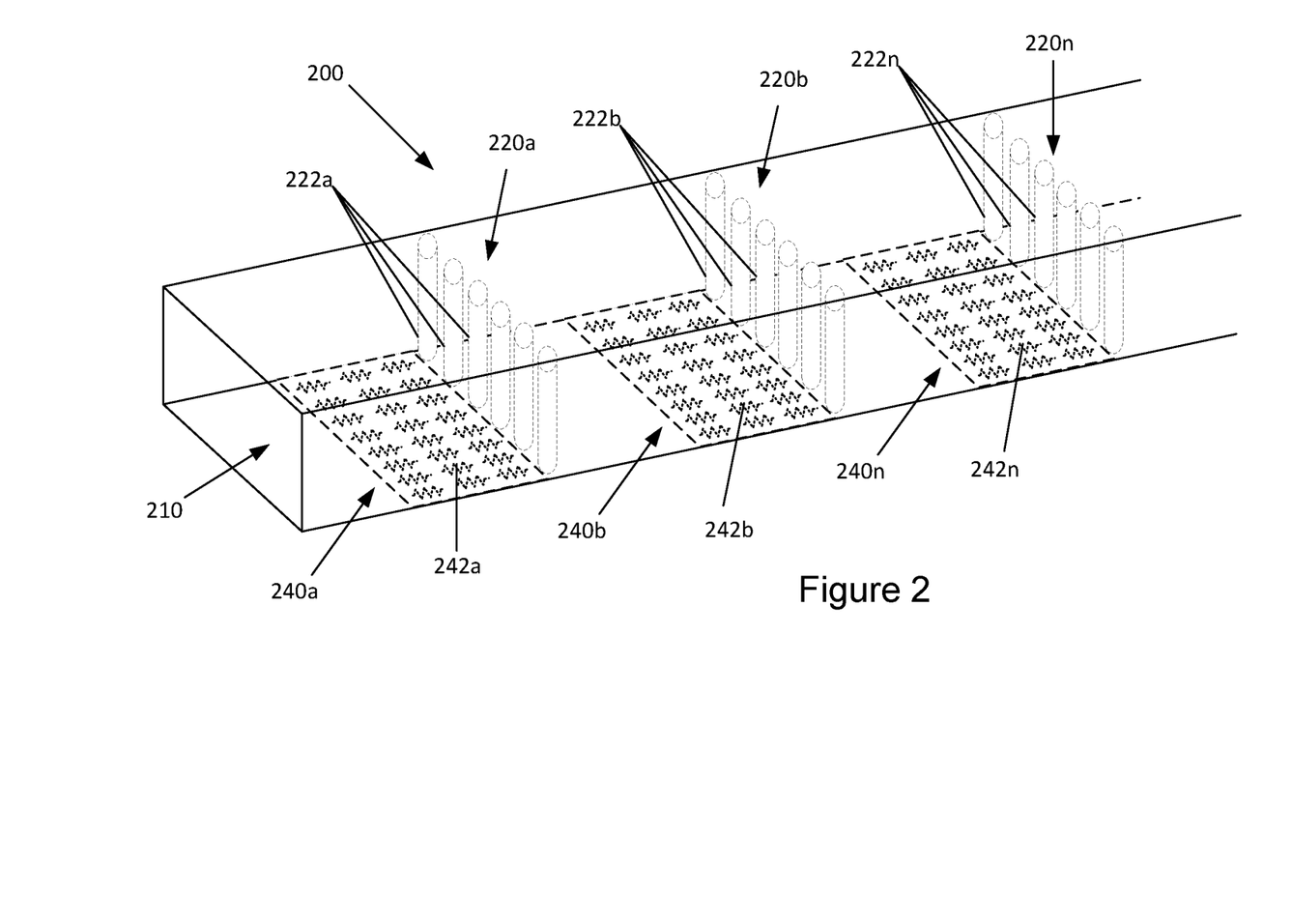
FIGS. 2-4 illustrate perspective views of other example systems.

Referring now to FIG. 2, a perspective view of another example system 200 is illustrated. The example system 200 is similar to the example system 100 of FIG. 1 and includes a microfluidic cavity 210. As noted above, the microfluidic cavity 210 may be a microfluidic channel. The example system 200 of FIG. 2 further includes an array of retaining features 220a-n and an array of releasing features 240a-n. As noted above, each retaining feature 220a-n is provided to position capsules (not shown in FIG. 2) at a predetermined location in the microfluidic cavity 210. In the example system 200 of FIG. 2, each retaining feature 220a-n includes a set of pillars 222a-n. In one example, the pillars 222a-n extend the entire height of the microfluidic cavity 210, as illustrated in FIG. 2. In other examples, the pillars 222a-n may extend up to a predetermined height that is less than the entire height of the microfluidic cavity 210.

The pillars 222a-n are separated by a gap between adjacent pillars 222. The size of the gap is selected to be sufficiently small to prevent the capsules from passing through. For example, the gap may be selected to be a size smaller than the diameter of the capsules. Further, the gap is sized to allow the material (e.g., antigens) enclosed in the capsules to pass through when the material is released from the capsules.

As noted above, each releasing feature 240a-n is provided to selectively cause degradation of the shell of the capsule by generating thermal energy. In various examples, as illustrated in FIG. 2, the releasing features 240a-n each include at least one resistor 242a-n. When activated, the resistors 242a-n generate heat to cause degradation of the thermally degradable shell of capsules positioned above the respective releasing feature 240. In some examples, each releasing feature 240a-n includes a single resistor. In other examples, as illustrated in FIG. 2, each releasing feature includes an array of resistors 242a-n. As described below with reference to FIGS. 11-12 and 14-16, thermal energy from the releasing features 240a-n causes degradation of the shell of the capsule, allowing the material enclosed in the shell to be released into the microfluidic cavity 210. In some examples, the resistors 242a-n may also cause the shell of the capsule to break via force generated with pulsing of the resistors 242a-n. Thus, the shell may be broken mechanically.

Figure 3:
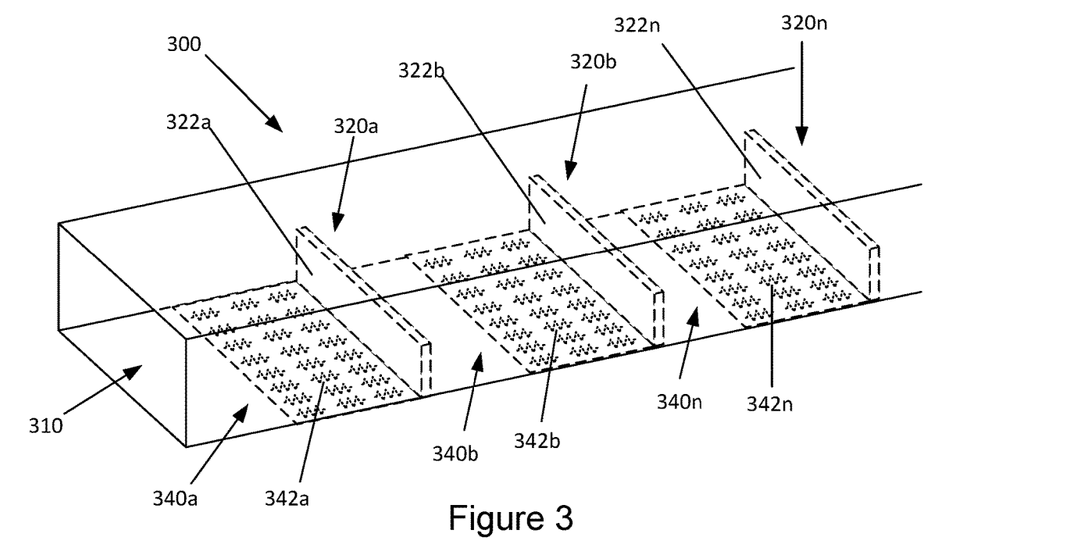

Referring now to FIG. 3, a perspective view of another example system 300 is illustrated. The example system 300 is similar to the example system 200 of FIG. 2 and includes a microfluidic cavity 310 and an array of releasing features 340a-n with an array of resistors 342a-n. The example system 300 of FIG. 3 further includes an array of retaining features 320a-n. In the example system 300 of FIG. 3, each retaining feature 320a-n includes a weir 322a-n. As illustrated in FIG. 3, each weir 322a-n extends substantially the entire width of the microfluidic cavity 310. In this regard, each weir 322a-n may be a wall that prevents capsules from passing to the sides of the weir 322a-n. As illustrated in the example of FIG. 3, each weir 322a-n extends only part of the height of the microfluidic cavity 310. Thus, capsules may be positioned as sediment in the predetermined position (e.g., above the releasing feature 340a-n). When the material within the capsules is released, the released material may pass over the weir 322a-n through the microfluidic cavity 310.

Figure 4:
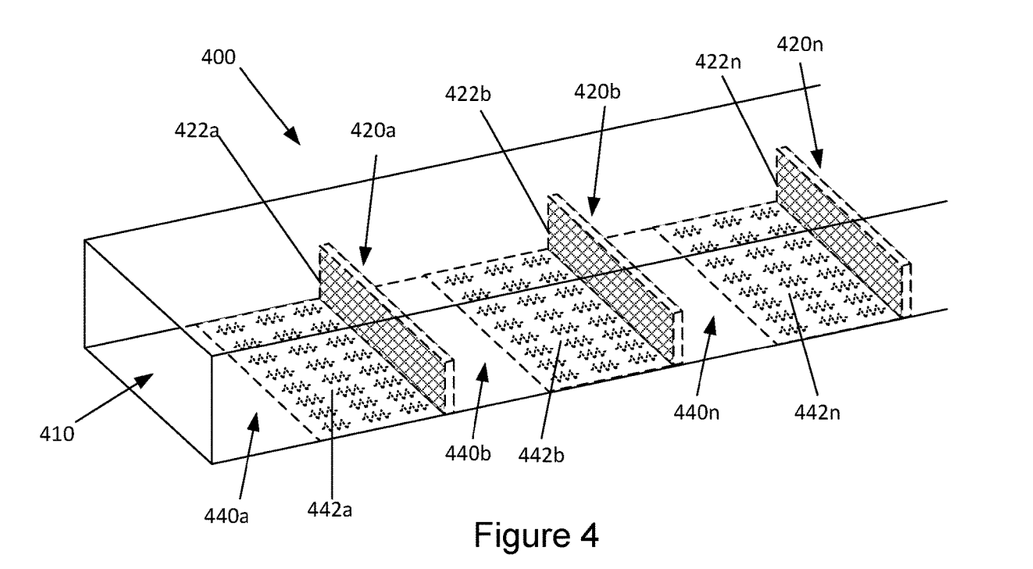

Referring now to FIG. 4, a perspective view of another example system 400 is illustrated. The example system 400 is similar to the example systems 200, 300 of FIGS. 2 and 3, respectively, and includes a microfluidic cavity 410 and an array of releasing features 440a-n with an array of resistors 442a-n. The example system 400 of FIG. 4 further includes an array of retaining features 420a-n. In the example system 400 of FIG. 4, each retaining feature 420a-n includes a mesh 422a-n. As illustrated in FIG. 4, each mesh 422a-n extends substantially the entire width of the microfluidic cavity 410 to prevent capsules from passing to the sides of the mesh 422a-n. As illustrated in the example of FIG. 4, each mesh 422a-n extends only part of the height of the microfluidic cavity 410. In other examples, the mesh 422a-n may extend the entire height of the microfluidic cavity 410.

In various examples, the mesh 422a-n is provided with openings that are smaller than the diameter of the capsules. Thus, the mesh 422 prevents the capsules from passing through. The openings are sufficiently large to allow the material encapsulated in the capsules from passing through when the material is released from the capsules.

Figure 5:
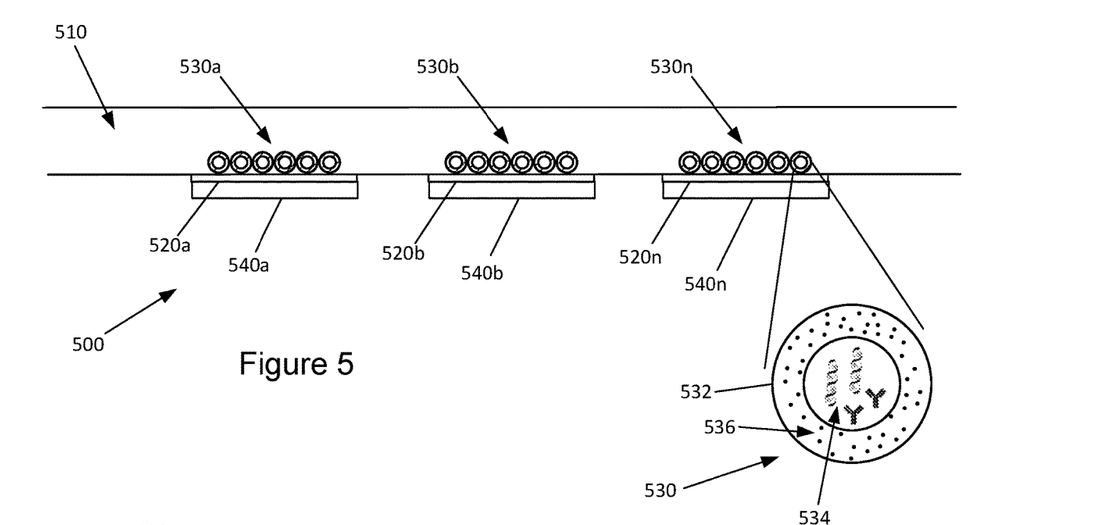
FIGS. 5-7 illustrate side views of other example systems.

Referring now to FIG. 5, a side view of another example system 500 is illustrated. The example system 500 of FIG. 5 includes a microfluidic cavity 510 which may accommodate particles or fluid therein. The example system 500 further includes an array of retaining features 520a-n for positioning capsules 530a-n in a predetermined location and an array of releasing features 540a-n to release material 534 encapsulated in a shell 532 of the capsules 530. In various examples, as described below with reference to FIGS. 8-10, each retaining feature 520a-n and corresponding releasing feature 540a-n may be provided to have capsules 530a-n with a different corresponding material 534 therein. Similar to the examples systems described above, each releasing feature 540a-n may include a resistor, or an array of resistors, to generate thermal energy to degrade the thermally degradable shell of the capsules 530a-n.

Each retaining feature 520a-n of the example system 500 of FIG. 5 includes a magnet (e.g., electromagnet) positioned above the corresponding releasing feature 540a-n. In this regard, the retaining feature 520a-n uses magnetic forces to selectively position the capsules 530a-n at the predetermined location in the microfluidic cavity 510. In the example system 500 of FIG. 5, the capsules 530 are provided with metal nanoparticles 536 embedded within the thermally degradable shell 532. Thus, as the capsules 530 are flowed through the microfluidic cavity, the metal nanoparticles 536 are attracted by the magnet of the retaining feature 520, thus positioning the capsules 530a-n at the corresponding retaining feature 520a-n.

Figure 6:
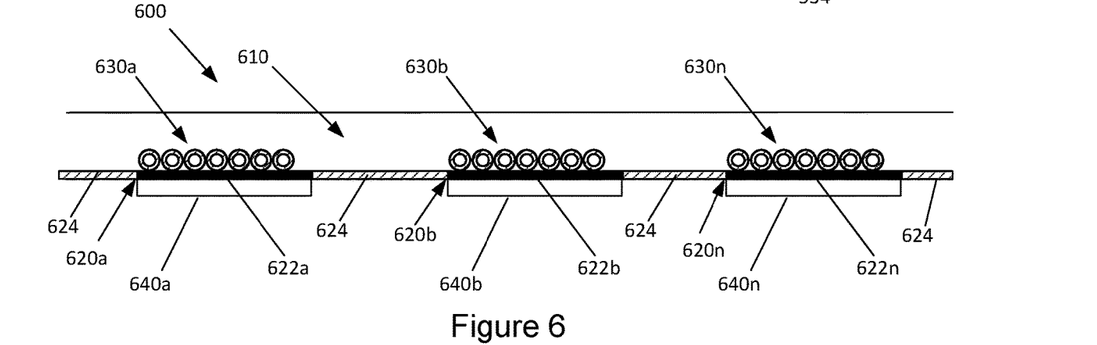

Referring now to FIG. 6, a side view of another example system 600 is illustrated. The example system 600 of FIG. 6 includes a microfluidic cavity 610 which may accommodate particles or fluid therein. The example system 600 further includes an array of retaining features 620a-n for positioning capsules 630a-n in a predetermined location and an array of releasing features 640a-n to release material encapsulated in a shell of the capsules 630a-n. Similar to the examples systems described above, each releasing feature may include a resistor, or an array of resistors, to generate thermal energy to degrade the thermally degradable shell of the capsules 630a-n.

Each retaining feature 620a-n of the example system 600 of FIG. 6 includes a hydrophobic surface 622a-n. The hydrophobic surface 622a-n has a low surface energy to which the thermally degradable material (e.g., wax) of the shell of the capsules attaches. In one example, as illustrated in FIG. 6, the hydrophobic surface 622a-n of each retaining feature 620a-n is surrounded by a hydrophilic surface 624. Thus, the difference in the surface energy between the hydrophobic surface 622a-n and the hydrophilic surface 624 is increased, enhancing the settling of the capsules 630a-n to the corresponding hydrophobic surface 622a-n.

Figure 7:
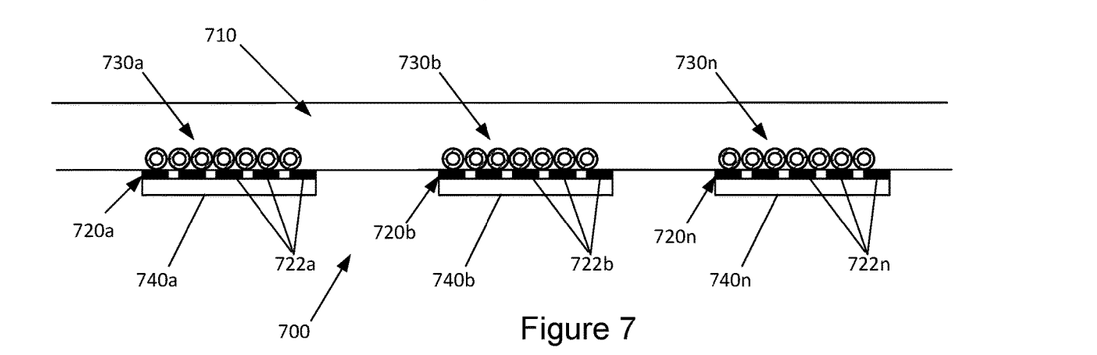

Referring now to FIG. 7, a side view of another example system 700 is illustrated. The example system 700 of FIG. 7 includes a microfluidic cavity 710 which may accommodate particles or fluid therein. The example system 700 further includes an array of retaining features 720a-n for positioning capsules 730a-n in a predetermined location and an array of releasing features 740a-n to release material encapsulated in a shell of the capsules 730a-n. Similar to the examples systems described above, each releasing feature may include a resistor, or an array of resistors, to generate thermal energy to degrade the thermally degradable shell of the capsules 730.

Each retaining feature 720a-n of the example system 700 of FIG. 7 includes a set of dielectrophoreses (DEP) electrodes 722a-n. The DEP force generated by the DEP electrodes 722a-n is selected to be sufficient to attract the capsules 730a-n. The DEP electrodes 722a-n are spaced apart within the predetermined location at which the capsules 730 are to be positioned.

Figure 8:
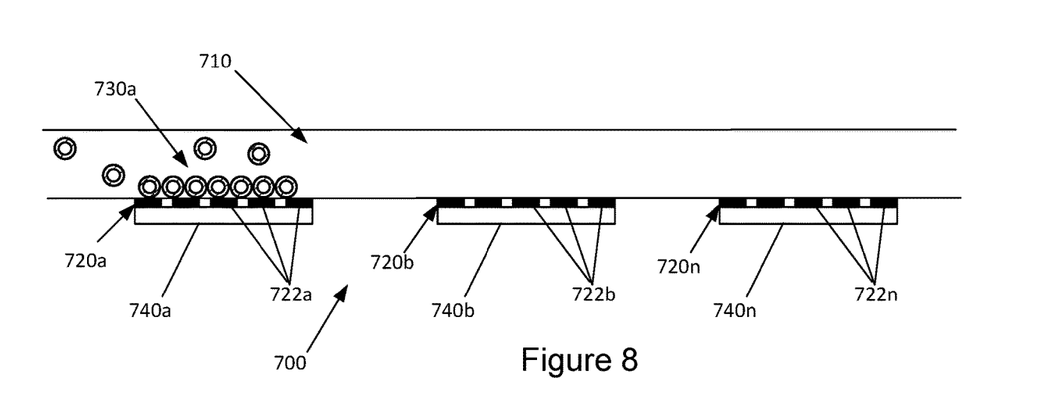
FIGS. 8-10 illustrate configuring of the example system of FIG. 7 with selected capsules.
Figure 9:
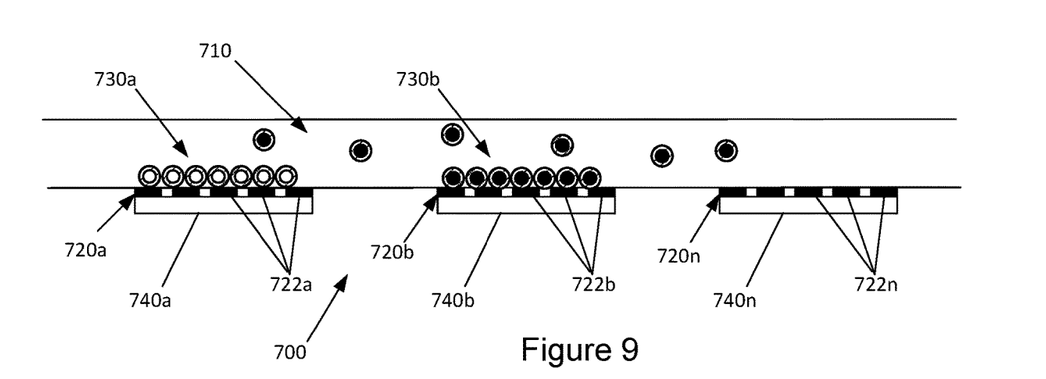
Figure 10:
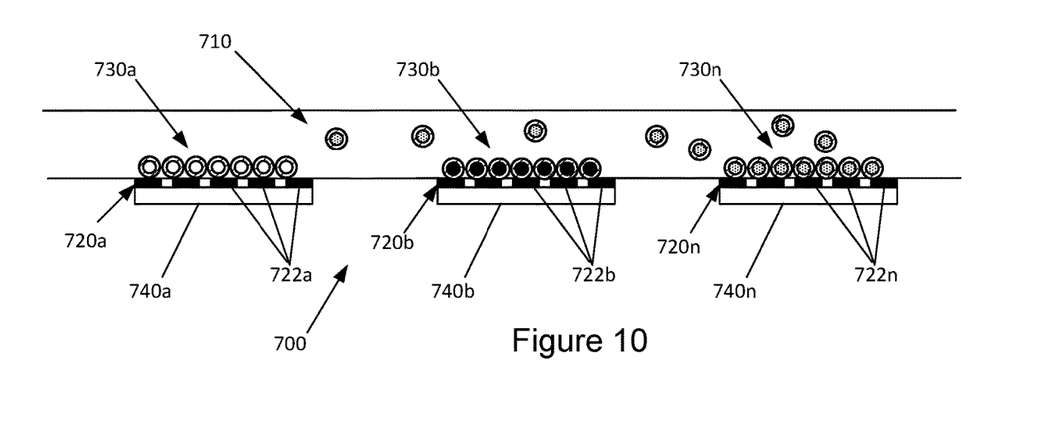

Referring now to FIGS. 8-10, configuring of the example system of FIG. 7 with selected capsules is illustrated. The example system 700 may be provided with no capsules included and may serve as a template or a blank that may be configurable by the user. In this regard, the user may select capsules with desired material (e.g., reagent, nucleic acid segment, antibody, etc.) enclosed in a thermally degradable shell. In various examples, the system 700 may be provided with any practical number (n) of retaining features 720 and releasing features 740. In this regard, the user may select n different types of capsules, each corresponding to one retaining feature 720 in the array of retaining features.

Referring now to FIG. 8, a user may select a first material in the capsule (e.g., a first type of antibody) and flow capsules with the selected material through the microfluidic cavity 710. The user, or a controller coupled to the example device 700, may activate the DEP electrodes 722a corresponding to a selected retaining feature 720. The DEP force generated by the DEP electrodes 722a causes at least some of the capsules 730a flowing through the microfluidic cavity 710 to be retained at the predetermined location (e.g., above the releasing feature 740a). In some examples, once sufficient number of capsules 730a are retained at the retaining feature 720a, the DEP electrodes 722a associated with the first retaining feature 720a may be deactivated. The process may then be repeated for capsules with additional types of materials enclosed. For example, as illustrated in FIG. 9, a second set of capsules 730b is flowed through the microfluidic cavity 710, and a different set of DEP electrodes 722b are activated. Again, the DEP force generated by the DEP electrodes 722b causes at least some of the capsules 730b flowing through the microfluidic cavity 710 to be retained at the predetermined location (e.g., above the releasing feature 740b). FIG. 10 illustrates the process being repeated for the nth set of capsules 730n, which are retained at the nth retaining feature 720n.

Figure 11:
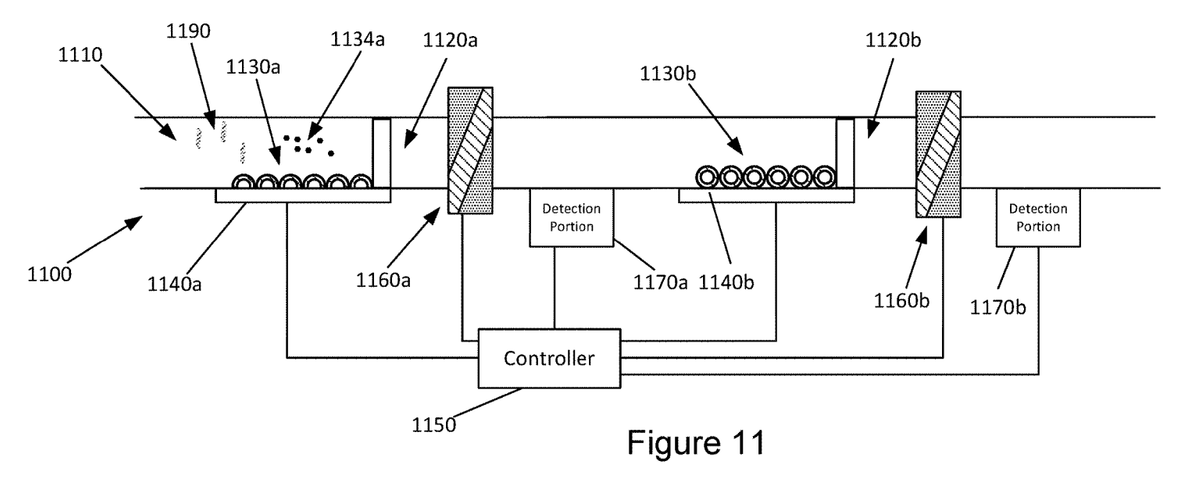
FIGS. 11 and 12 illustrate an example system for amplification and detection of a nucleic acid segment.
Figure 12:
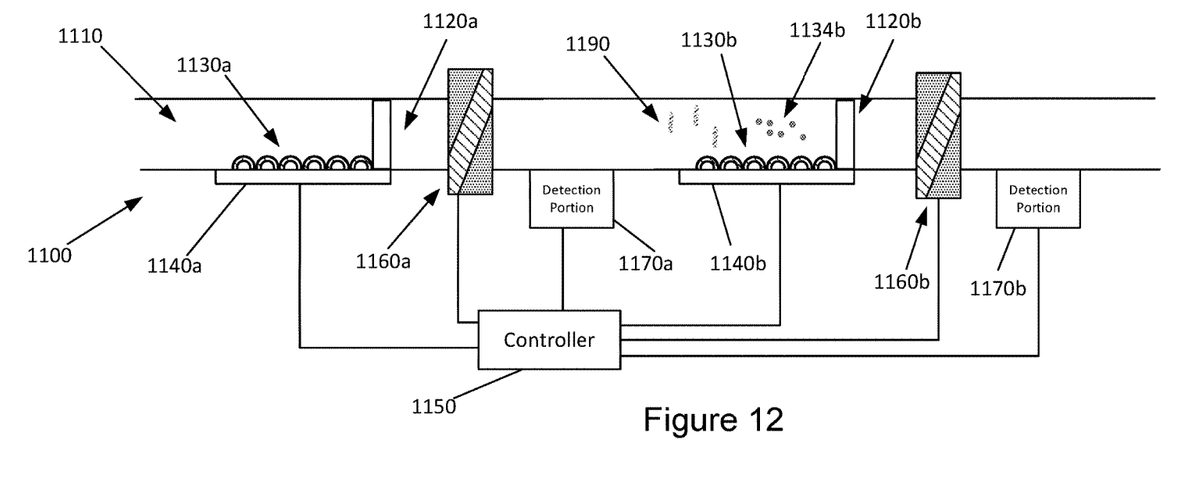

Referring now to FIGS. 11 and 12, an example system 1100 for amplification and detection of a nucleic acid segment is illustrated. Like the various example systems described above, the example system 1100 of FIGS. 11 and 12 includes a microfluidic cavity 1110, an array of retaining features 1120a,b, and an array of corresponding releasing features 1140a,b. Each retaining feature 1120a,b is provided to position corresponding capsules 1130a,b at a predetermined location in the microfluidic cavity 1110. In the example illustrated in FIGS. 11 and 12, each retaining feature 1120a,b is provided with capsules 1130a,b containing a corresponding type of reagent. A controller 1150 is coupled to each releasing feature 1140a,b to selectively activate each releasing feature 1140a,b to generate thermal energy to degrade the shell of the corresponding capsules 1130a,b.

The example system 1100 of FIGS. 11 and 12 is further provided with a thermocycling portion 1160a,b corresponding to each releasing feature 1140a,b. In various examples, the thermocycling portion 1160a,b is provided to cause amplification of a nucleic acid segment. The amplification is facilitated by a reagent released from the capsules 1130a,b. In this regard, the temperature in the thermocycling portion 1160a,b is actively cycled through various temperatures to facilitate amplification of the nucleic acid segments. The temperature profile in the thermocycling portion 1160a,b may be selected for particular applications. In one example, the temperature profile in the thermocycling portion 1160a,b includes a denaturation step with the temperature at about 95 C followed by a primer annealing step at about 65 C and a primer extension step at about 73 C. Material in the thermocycling portion 1160a,b may be exposed to numerous cycles of the temperature profile. In one example, the material may be exposed to between about 25 and about 50 cycles of the temperature profile, with each step in each cycle lasting between about 1 millisecond and about 20 minutes. In one example, each step in each cycle lasts about 2 minutes.

The example system 1100 is further provided with a detection portion 1170a,b corresponding to each thermocycling portion 1160a,b. As illustrated in the example of FIGS. 11 and 12, the controller 1150 is coupled to a corresponding releasing feature 1140a,b, a corresponding thermocycling portion 1160a,b, and a corresponding detection portion 1170a,b.

As illustrated in the example of FIG. 11, a nucleic acid segment 1190 is flowed through the microfluidic cavity 1110. In various examples, the nucleic acid segment 1190 may be provided in an aqueous solution. In response to the release of the nucleic acid segment 1190, the controller 1150 activates the first releasing feature 1140a to generate thermal energy. The thermal energy causes the shell of the capsules to degrade, resulting in release of a reagent 1134a into the microfluidic cavity 1110. The reagent 1134a and the nucleic acid segment 1190 are then passed through the thermocycling portion 1160a corresponding to the first releasing feature 1140a. If the nucleic acid segment 1190 corresponds to the first reagent 1134a, the addition of the first reagent 1134a to the flow causes amplification of the nucleic acid segment 1190. The amplified nucleic acid segment 1190 would then be detectable by the detection portion 1170a. The controller 1150 may then receive a signal from the detection portion 1170a, allowing the controller 1150 to determine whether the detection portion 1170a detected the amplified nucleic acid segment.

Referring now to FIG. 12, the nucleic acid segment 1190 may continue to flow through the microfluidic cavity 1110, and the controller may repeat the process with additional releasing features, such as releasing feature 1140b. Activation of the second releasing feature causes thermal energy to degrade the shell of the second capsules 1130*b*, thus releasing a second reagent 1134*b* into the microfluidic cavity 1110. In various examples, the second reagent 1134*b* is different from the first reagent 1134*a*. In this regard, each reagent 1134*a,b* may be selected to facilitate amplification of a specific nucleic acid segment 1190. Thus, each thermocycling portion 1160*a,b* may amplify the nucleic acid segment if the nucleic acid segment corresponds to the reagent 1134*a,b* associated with the thermocycling portion 1160*a,b*.

Figure 13:
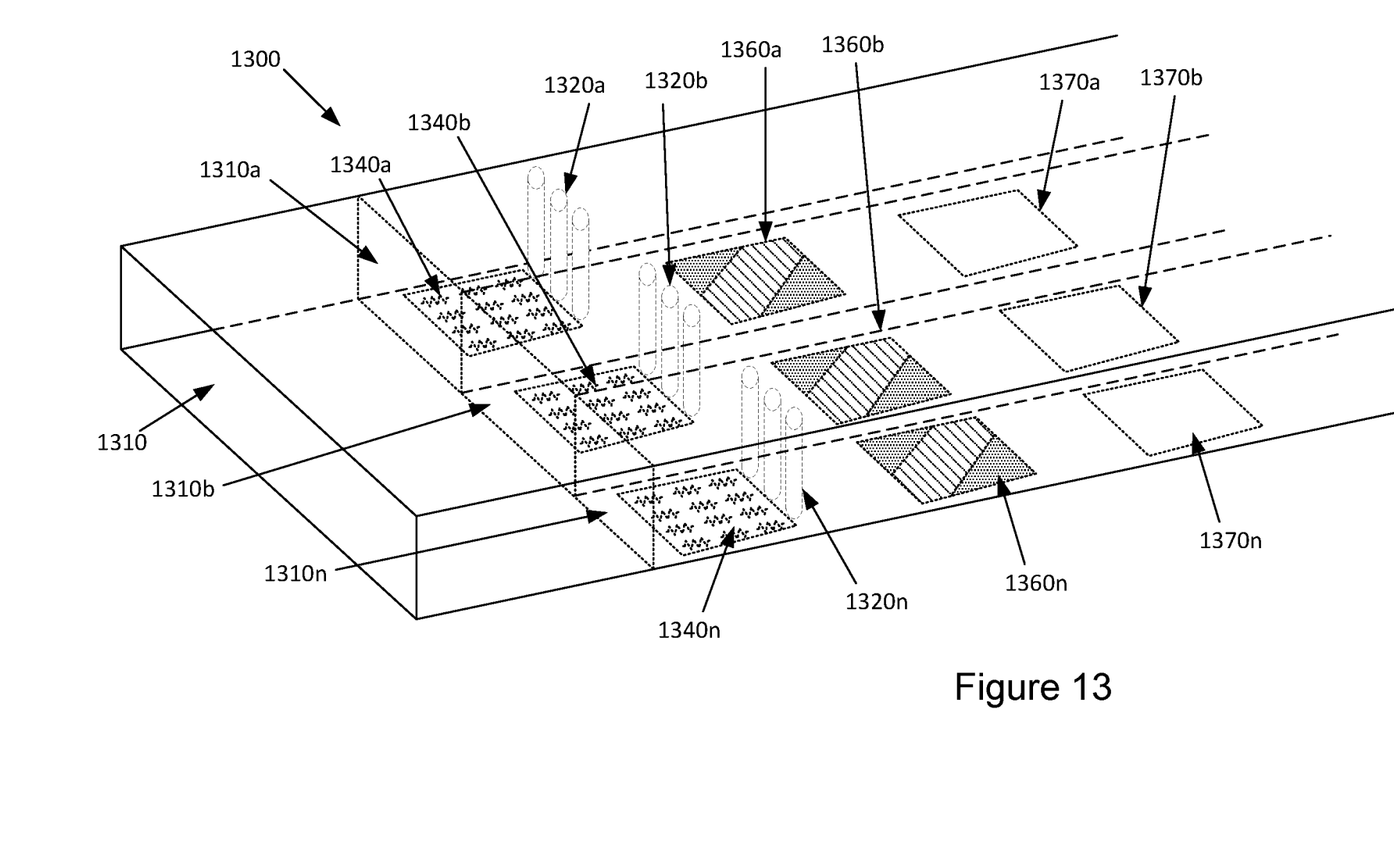
FIG. 13 illustrated another example system for amplification and detection of a nucleic acid segment.

Referring now to FIG. 13, another example system for amplification and detection of a nucleic acid segment is illustrated. In this regard, while the example system 1100 described above with reference to FIGS. 11 and 12 processes the nucleic acid segment with different reagents in a sequential manner, the example system 1300 of FIG. 13 allows the various reagents to be released in a parallel manner. In this regard, the example system 1300 is provided with a microfluidic cavity 1310 into which a nucleic acid segment is released. The microfluidic cavity 1310 branches into multiple channels 1310*a-n*. Each channel 1310*a-n* includes a corresponding retaining feature 1320*a-n*, releasing feature 1340*a-n*, thermocycling portion 1360*a-n*, and corresponding detection portion 1370*a-n*. Thus, the nucleic acid segment may be tested with numerous reagents simultaneously.

Figure 14:
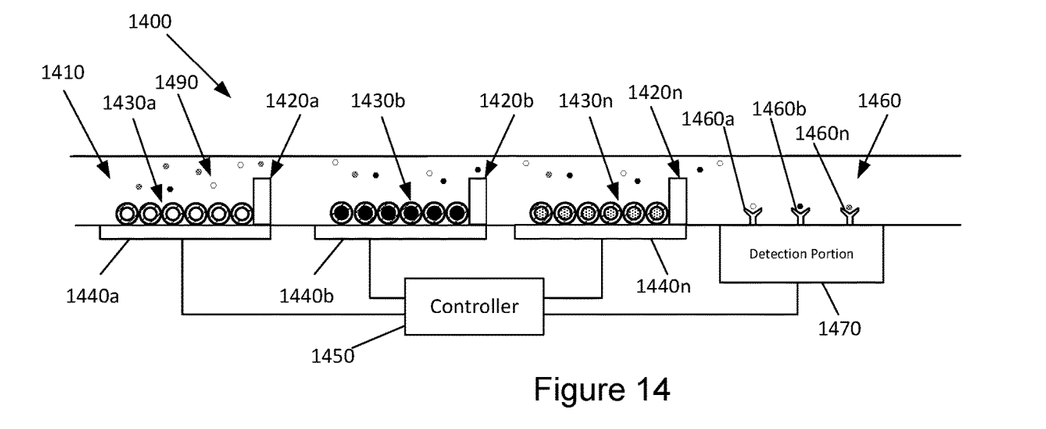
FIGS. 14-16 illustrate an example system for detection of an antigen.
Figure 15:
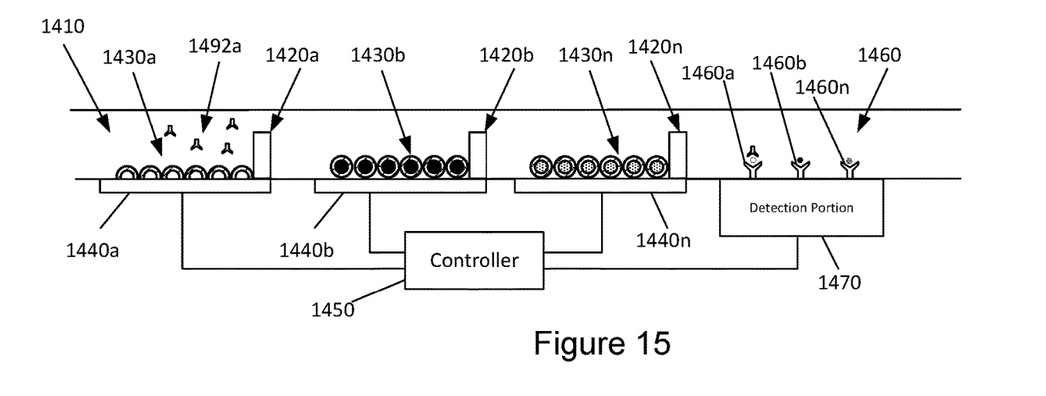
Figure 16:
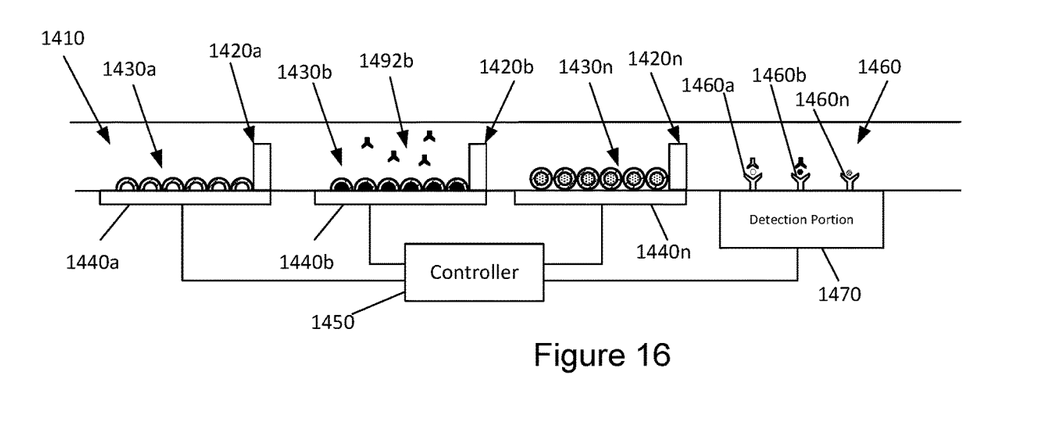

Referring now to FIGS. 14-16, an example system 1400 for detection of an antigen is illustrated. Like the various example systems described above, the example system 1400 of FIGS. 14-16 includes a microfluidic cavity 1410, an array of retaining features 1420*a-n* and an array of corresponding releasing features 1440*a-n*. Each retaining feature 1420*a-n* is provided to position corresponding capsules 1430*a-n* at a predetermined location in the microfluidic cavity 1410. In the example illustrated in FIGS. 14-16, each retaining feature 1420*a-n* is provided with capsules 1430*a-n* containing a corresponding type of primary antibody. A controller 1450 is coupled to each releasing feature 1440*a-n* to selectively activate each releasing feature 1440*a-n* to generate thermal energy to degrade the shell of the corresponding capsules 1430*a-n*.

The example system 1400 is further provided with an array of immobilized secondary antibodies 1460*a-n*. In one example, the array of immobilized secondary antibodies 1460*a-n* may be an array of regions with each region containing secondary antibodies of a specific type. In one example, each immobilized secondary antibody 1460*a-n* is associated with a primary antibody in a corresponding capsule 1430*a-n*. The primary antibodies in the capsules 1430*a-n* and the immobilized secondary antibodies 1460*a-n* may bind to various antigens, as illustrated below. The example system 1400 is further provided with a detection portion 1470 to detect or determine whether an antigen is binded to any of the immobilized secondary antibodies 1460*a-n*.

FIGS. 14-16 illustrate an example operation of the example system 1400 to detect the presence of antigens. As illustrated in FIG. 14, a set of antigens 1490 is released into the microfluidic cavity 1410. The antigens 1490 are allowed to pass through to the array of immobilize secondary antibodies 1460*a-n*. In this regard, the retaining features 1420*a-n* may be sized to allow passing through of antigens 1490*a-n*. Various antigens 1490*a-n* may bind to corresponding immobilized secondary antibodies 1460*a-n*, as illustrated in FIG. 14.

The controller 1450 may then sequentially activate each releasing feature 1440*a-n*, as illustrated in FIGS. 15 and 16. First referring to FIG. 15, the controller 1450 activates the first releasing feature 1440*a*, thus generating thermal energy to degrade the shell of the capsules 1430*a*. The primary antibodies 1492*a* in the first set of capsules 1430*a* are then released into the microfluidic cavity 1410 and can flow downstream (to the right in FIGS. 14-16). The primary antibodies 1492*a* in the first set of capsules 1430*a* may be selected to bind a specific antigens. Thus, if the specific antigen or antigens are binded to the immobilized secondary antibodies 1460*a-n*, the primary antibodies 1492*a* will bind to the antigens at the immobilized secondary antibodies 1460*a-n*. In the example of FIG. 15, the primary antibodies 1492*a* are shown binded to an antigen which is binded to the first immobilized secondary antibody 1460*a*.

In various examples, the primary antibodies 1492*a* may include a characteristic that is detectable by the detection portion 1470. For example, the detection portion 1470 may detect florescence or other such characteristic if the primary antibody is present at any of the immobilized secondary antibodies 1460*a-n*. Thus, the controller may detect the presence of the first primary antibody 1492*a* at the first immobilized secondary antibody 1460*a*. In one example, an agent may be flowed through the microfluidic channel to remove the detectable characteristic prior to release of subsequent primary antibodies. For example, the fluorophore on the first primary antibody binded to the first immobilized secondary antibody 1460*a* may be removed with a photobleach, for example.

The controller may then repeat the process with subsequent releasing features 1440*b-n*. For example, FIG. 15 illustrates the activation of the second releasing feature 1440*b* and release of second primary antibodies 1492*b*, which are shown as binded to the second immobilized secondary antibody 1460*b*.

In the example illustrated in FIGS. 14-16, the number of components in each array is shown as n. It will be understood that, in various examples, n may be any practical number. Further, the number of immobilized secondary antibodies 1460 may be different than the number of retaining feature 1420, the number of releasing features 1440 or the number of types of primary antibodies 1492.

Figure 17:
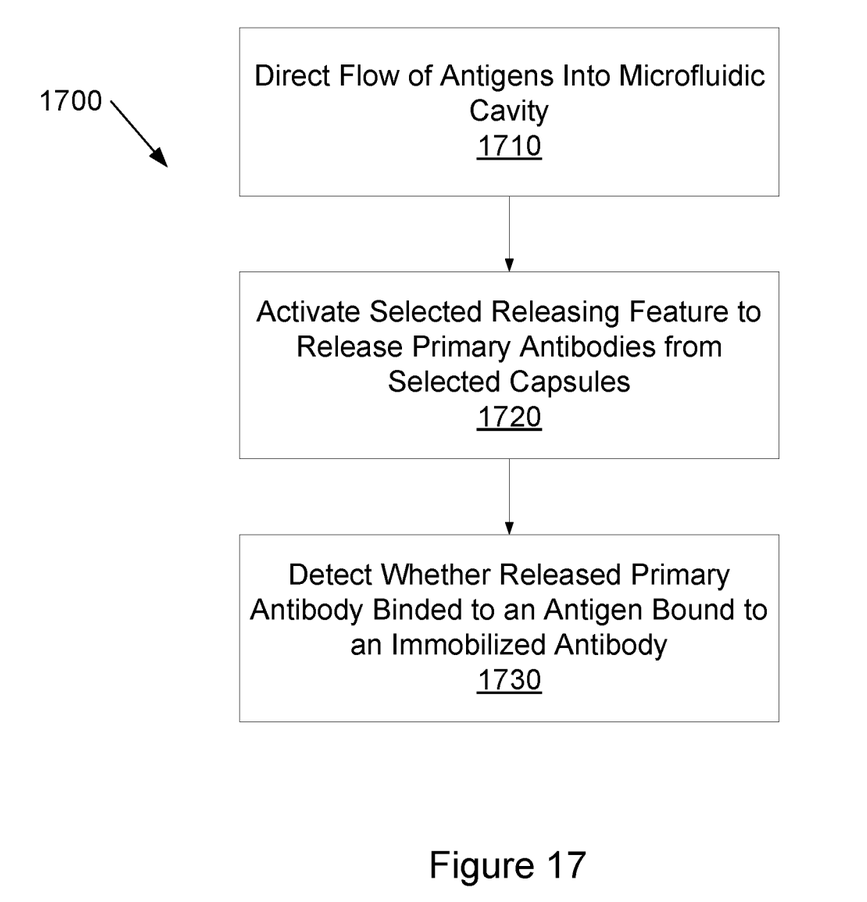
FIG. 17 is a flow chart illustrating an example method for detection of an antigen.

Referring now to FIG. 17, a flow chart illustrating an example method 1700 for detection of an antigen is illustrated. The example method 1700 may be implemented, for example, in the system 1400 described above with reference to FIGS. 14-16. The example method 1700 includes directing a flow of antigens into a microfluidic cavity (block 1710). For example, as described above, the antigens 1490 may be flowed into the microfluidic cavity 1410 of the example system 1400. The antigens are flowed to an array of immobilized antibodies, such as the immobilized secondary antibodies 1460*a-n*. The antigens may include different types of antigens, and the array of immobilized antibodies may include different types of immobilized antibodies. Each type of immobilized antibody may be selected to bind to a corresponding antigen.

The example method 1700 further includes activating a selected releasing feature from an array of releasing features to release primary antibodies contained in capsules (block 1720). As described above, the selected releasing feature corresponds to a capsule with a selected primary antibody. The capsule has a thermally degradable shell (e.g., wax or polymer) enclosing the selected primary antibody therein.

The example method 1700 further includes detecting whether the released selected primary antibody is binded to at least one antigen binded to the selected immobilized antibody (block 1730). As described above, if an antigen associated with the primary antibody is binded to an immobilized antibody, the primary antibody may bind to the antigen at the immobilized antibody. A fluorophore on the primary antibody may be detected by a detection portion provided proximate to the immobilized antibodies.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. A system, comprising:
   an array of retaining features, each retaining feature in the array of retaining features being configured to position capsules at a predetermined location, the capsules having a thermally degradable shell enclosing a primary antibody selected from a set of primary antibodies therein;
   an array of thermally controlled releasing features, each releasing feature in the array of releasing features corresponding to a retaining feature in the array of retaining features, each releasing feature being configured to selectively cause degradation of the shell of a capsule to release the primary antibody, each releasing feature to generate thermal energy to facilitate degradation of the shell;
   an array of immobilized secondary antibodies including at least two types of secondary antibodies, each type of secondary antibody corresponding to a primary antibody; and
   a detection portion to detect a primary antibody bound to an antigen, the antigen being bound to a secondary antibody in the array of immobilized secondary antibodies.

2. The system of claim 1, further comprising a controller to:
   (a) release set of antigens to pass through the array of immobilized secondary antibodies, the set of antigens including different types of antigens, each type of antigen to bind with a corresponding type of secondary antibody;
   (b) activating a selected releasing feature from the array of thermally controlled releasing features, the selected releasing feature corresponding to a capsule with a selected primary antibody corresponding to a selected type of secondary antibody; and
   (c) detecting the presence or absence of the selected primary antibody bound to an antigen bound to the selected type of secondary antibody to determine presence or absence of the type of antigen.

3. The system of claim 1, wherein each releasing feature is a resistor to generate the thermal energy when activated.

4. The system of claim 1, wherein the thermally degradable shell is formed of a wax or polymer material.

5. A method, comprising:
   directing a flow of antigens to an array of immobilized antibodies, the flow of antigens including different types of antigens, the array of immobilized antibodies including different types of immobilized antibodies, each type of immobilized antibody to bind to a corresponding antigen;
   activating a selected releasing feature from an array of thermally controlled releasing features, the selected releasing feature corresponding to a capsule with a selected primary antibody, the capsule having a thermally degradable shell enclosing the selected primary antibody therein, wherein activation of the selected releasing feature causes the selected primary antibody to be released from the shell of the capsule; and
   detecting whether the released selected primary antibody is bound to at least one antigen bound to the selected immobilized antibody.

6. The method of claim 5, further comprising:
   repeating the activating and detecting for an additional type of immobilized antibody.

7. The method of claim 5, further comprising positioning capsules at the array of thermally controlled releasing features, wherein the positioning comprises:
   flowing capsules with a selected type of primary antibody to the array of thermally controlled releasing features, each releasing feature in the array of thermally controlled releasing features including a dielectrophoreses electrode; and
   activating the dielectrophoreses electrode corresponding to a selected releasing feature in the array of thermally controlled releasing features, activation of the dielectrophoreses electrode causing capsules with the selected type of primary antibody to be attracted to the selected releasing feature.

8. The method of claim 5, wherein each releasing feature is a resistor to generate the thermal energy when activated.

9. The system of claim 1, wherein the retaining feature includes at least one of a set of pillars, a weir, a mesh, a magnetic portion, a hydrophobic region surrounded by hydrophylic regions, or dielectrophoreses electrodes.

10. The system of claim 1, wherein the array of retaining features include or are associated with a first set of dielectrophoreses electrodes that are deactivatable to release at least some of the capsules from the predetermined location.

11. The system of claim 10, further comprising a second set of dielectrophoreses electrodes to interact with capsules after deactivation of the dielectrophoreses electrodes.

12. The system of claim 1, wherein the releasing feature is a resistor that generates heat when activated.

13. The system of claim 2, further comprising (d) repeating (b) and (c) for additional types of secondary antibodies.

14. The method of claim 5, wherein in addition to the thermally controlled releasing features, releasing features include a set of pillars, a weir, a mesh, a magnetic portion, a hydrophobic region surrounded by hydrophyllic regions, or dielectrophoreses electrodes.

15. The method of claim 7, further comprising repeating the flowing and activating for additional types of primary antibodies.

* * * * *